United States Patent [19]
Eck et al.

[11] 3,932,408
[45] Jan. 13, 1976

[54] PYRIMIDINES AND PROCESS OF MAKING THE SAME

[75] Inventors: Herbert Eck, Burghausen Burg; Frank Muller, Siegertsbrunn; Sven E. Wihrheim, Furstenfeldbruck, all of Germany

[73] Assignee: Wacker-Chemie GmbH, Munich, Germany

[22] Filed: Dec. 19, 1973

[21] Appl. No.: 426,419

[30] Foreign Application Priority Data
Dec. 22, 1972 Germany.............................. 2263052

[52] U.S. Cl. ........................ 260/256.4 N; 424/251
[51] Int. Cl.² ..................................... C07D 239/30
[58] Field of Search .............................. 260/256.4 N

[56] References Cited
UNITED STATES PATENTS
3,703,517  11/1972  Kim et al. .................... 260/256.4 N OTHER PUBLICATIONS
Bates, "Chemical Abstracts," Vol. 65, 1964.
Vincze, et al., "Chemical Abstracts," Vol. 66, 1967.

*Primary Examiner*—Richard J. Gallagher
*Assistant Examiner*—James H. Turnipseed
*Attorney, Agent, or Firm*—Allison C. Collard

[57] ABSTRACT

A compound of the formula

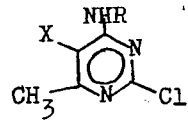

wherein X is a member of the group consisting of H and Br, and R is a member of the group consisting of straight-chain and branched-chain alkyl radicals and cycloalkyl radicals having from 5 – 8 C-atoms. The invention also relates to the preparation of the new compounds. The pyrimidines of the invention are useful pesticides, particularly herbicides and fungicides.

1 Claim, No Drawings

PYRIMIDINES AND PROCESS OF MAKING THE SAME

This invention relates to new pyrimidines of the general formula

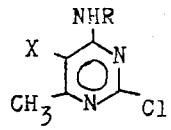

wherein X is a member of the group consisting of H and Br, and R is a member of the group consisting of straight-chain and branched-chain alkyl radicals and cycloalkyl radicals having from 5 – 8 C-atoms. The invention also relates to the preparation of the new compounds.

The following compounds are mentioned by way of example:
4-(1,2-dimethylpropylamino)-2-chloro-6-methyl-pyrimidine
4-(1,3-dimethylbutylamino)-2-chloro-6-methyl-pyrimidine
4-(1,3-dimethylpentylamino)-2-chloro-6-methyl-pyrimidine
4-(2-ethylhexylamino)-2-chloro-6-methylpyrimidine
4-cyclohexylamino-2-chloro-6-methylpyrimidine
4-(1,2-dimethylpropylamino)-5-bromo-2-chloro-6-methylpyrimidine
4-(1,3-dimethylbutylamino)-5-bromo-2-chloro-6-methylpyrimidine
4-(1,3-dimethylpentylamino)-5-bromo-2-chloro-6-methylpyrimidine
4-(2-ethylhexylamino)-5-bromo-2-chloro-6-methylpyrimidine
4-cyclohexylamino-5-bromo-2-chloro-6-methylpyrimidine Pyrimidines or their hydrobromides of the general formula

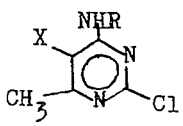

are made by reacting a solution of 2,4-dichloro-6-methylpyrimidine with 1.8–2.2 times the molar amount of the appropriate amine, at −30° to 80°C, preferably −15° to 30°C. The aminohydrochloride obtained is withdrawn from the reaction mixture and the isomers formed are separated by fractional distillation in vacuo. In the case where X stands for Br, bromination is carried out with 0.95 to 1.1 mol bromine per mol pyrimidine in the presence of chlorinated hydrocarbons or low-molecular carboxylic acids at 0° – 80°C, preferably at 20° – 50°C.

Suitable solvents for the reaction of the 2,4-dichloro-6-methylpyrimidine with the required amine for instance: chlorinated hydrocarbons, such as chlorobenzene, dichlorobenzenes, water, lower alcohols, if desired in mixture with water, e.g. methanol, ethanol, butanol, propanol; the reaction medium or the reaction product may likewise be used.

Suitable solvents for the separation of 2-chloro-4-amino-, as well as 4-chloro-2-amino-6-methylpyrimidine are e.g. chlorinated hydrocarbons such as carbon tetrachloride, chloroform, methylene chloride, hydrocarbons, such as benzene and toluene; also ether, e.g. diethyl ether, dibutyl ether, and tetrahydro furane.

Suitable solvents for the bromination are halogenated hydrocarbons, e.g. carbon tetrabromide or carbon tetrachloride, chloroform, methylene chloride and low-molecular aliphatic carboxylic acids, such as acetic or propionic acids.

The pyrimidines of the formula

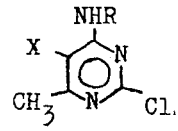

or their hydrobromides are useful pesticides, particularly herbicides and fungicides.

When the compounds according to the invention have herbicidal properties, they are effective in after-germination and have a pronounced selectivity to useful grains and kale plants. However, they destroy weeds, e.g. crab grass, wild oats and the other broad-leafed weeds.

The effective agents can be worked up to emulsion concentrates, spraying powders and dusting powders in a conventional manner.

In the following, a number of examples will be given for the description of the herbicides and their preparation according to the invention, but it should be understood that these are for illustration only, and not by way of limitation.

Preparation of the products according to the invention:

EXAMPLES 1–5

1.5 mol (245 g) of 2,4-dichloro-6-methylpyrimidine are dissolved in 1 liter ethanol and thereto are added drop by drop, 3 mols of the required amine in the course of about one hour. The reaction is exothermic. After the addition of the amine, the mixture remained standing at room temperature for about 3 days. The solvent was distilled off at 10 mm Hg; to the residue, chloroform and water were added, and the aminohydrochloride separated as an aqueous layer. The organic phase was dried with sodium sulfate or potassium carbonate, the solvent withdrawn, and the residue fractionated in vacuo. Obtained was the desired isomer A

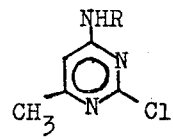

By-product Isomer B

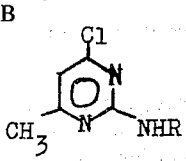

The structures were determined by NMR-spectroscopy.

Table 1

| Compound No.* | Radical R in Formula A and B | React. Tem. °C | Isomer A B.p. Yield °C mm Hg | | | Isomer B Byproduct) B.p. Yield °C mm Hg | | | Analysis (%) | | | |
|---|---|---|---|---|---|---|---|---|---|---|---|---|
| | | | | | | | | | C | H | N | Cl |
| 1 | —CH(CH₃)CH(CH₃)₂ | 0–10° | 50% | 135–138° | 0,15 | 19% | 90–100° | 0,15–0,4 | ** 56,20 | 7,55 | 19,66 | 16,59 |

Table 1-continued

| Compound No.* | Radical R in Formula A and B | React. Tem. °C | Isomer A Yield | B.p. °C mm Hg | Isomer B Byproduct) Yield | B.p. °C mm Hg | | Analysis (%) C | H | N | Cl |
|---|---|---|---|---|---|---|---|---|---|---|---|
| 2 | —⟨H⟩ | 0–5° | 48% | 152–156° 0,1 | 16% | 112–115° 0,1 | * A55,3<br>* B55,1<br>** 58,50 | 7,3<br>8,1<br>7,16 | 20,0<br>19,5<br>18,62 | 17,1<br>18,2<br>15,72 |
| 3 | —CH(CH₃)CH₂CH(CH₃)₂ | 50° | 60% | 137° 0,4 | 22% | 111–117° 0,5–1,2 | * A57,31<br>* B58,24<br>** 58,01<br>* A57,6 | 7,24<br>6,61<br>7,97<br>7,9 | 18,38<br>17,82<br>18,45<br>18,2 | 17,68<br>17,02<br>15,57<br>15,5 |
| 4 | —CH(CH₃)CH₂CH—C₂H₅<br>       \|<br>       CH₃ | 40° | 55% | 130–140° 0,2 | 30% | 105–108° 0,2 | * B56,7<br>** 59,61 | 8,1<br>8,34 | 20,1<br>17,38 | 15,6<br>14,67 |
| 5 | —CH₂CH(C₂H₅)(CH₂)₃CH₃ | 0–10° | 48% | 154–160° 0,06 | 30% | 100–130° 0.05 | * A58,8<br>* B57,1<br>** 61,02<br>* A59,44<br>* B61,27 | 8,4<br>8,0<br>8,67<br>8,51<br>8,51 | 19,4<br>17,8<br>16,45<br>17,11<br>16,47 | 14,67<br>17,1<br>13,86<br>14,96<br>14,08 |

*The numbers of the compound refer only to Isomers A
\* = Found
\*\* = Calc.

Preparation of 2-chloro-4-amino-5-bromo-6-methylpyrimidines:

0.05 mol of the desired 2-chloro-4-amino-5-bromo-6-methylpyrimidine were dissolved in 50 ml carbon tetrachloride and thereto are added drop by drop within about ¾ hour 0.05 mol bromine (8 g) dissolved in 10 ml carbon tetrachloride. In general, the reaction product was precipitated from the reaction solution in the form of crystals. The reaction temperature was 30°–40°C. There was an after-reaction for about 1.5 hours at 30°–40°C. The structures were determined by NMR-spectroscopy.

The yields, analyses and melting points of the obtained products can be seen from Table 2. In col. 2 of the table shows whether or not the product was precipitated from the reaction solution in the form of crystals.

IHS is a mixture of sodium alkyl-benzenesulfonate, alkylpolyglycol ether and solvent; IHS is a commercial name of Chemical Manufactureres Huls (Germany)

| B:Spraying Powder | |
|---|---|
| Effective Agent | 30 – 80% |
| Sodiumsulfosuccinic acid dioctylester | 2 – 3% |
| Sodium ligninsulfonate | 0 – 4% |
| Highly dispersed SiO₂ | 0 – 3% |
| Kaolin | 10 – 60% |

| C:Dusting Powder | |
|---|---|
| Effective Agent | 5 – 25% |
| Highly dispersed SiO₂ | 0 – 1% |
| Calcium Carbonate | 70 – 95% |

The wetting and dispersing agents used in combination with emulsion concentrates and spraying powders could be replaced by other suitable substances, e.g.

Table 2

| Compound No. | Radical R in the general formula<br>Br–[NHR/CH₃–N–Cl ring] · xHBr | crystals from re-action solutions | recrystalized from | % yield | melting point | | Analysis (%) C | H | N | Cl | Br | The analysis was calculated for |
|---|---|---|---|---|---|---|---|---|---|---|---|---|
| 6 | —CH(CH₃)CH₂CH(CH₃)₂ | yes | — | 45 | 136–138° | **<br>* | 34,09<br>29,32 | 4,68<br>4,27 | 10,84<br>— | 9,15<br>9,10 | 41,24<br>45,4 | C₁₁H₁₇N₃ClBr<br>·1 HBr* |
| 7 | —CH₂CH(C₂H₅)(CH₂)₃CH₃ | no | Butyl-acetate | 77 | 159–162° | **<br>* | 37,57<br>37,61 | 5,33<br>5,72 | 10,11<br>— | 8,53<br>8,54 | 38,46<br>38,40 | C₁₃H₂₁N₃ClBr<br>·1 HBr |
| 8 | —CH(CH₃)CH(CH₃)₂ | yes | acetic acid | 65 | 178°u.Z. | **<br>* | 26,41<br>27,14 | 3,77<br>3,84 | 9,25<br>— | 7,82<br>8,00 | 52,75<br>53,2 | C₁₀H₁₅N₃ClBr<br>·2 HBr |
| 9 | —⟨H⟩ | yes | — | 75 | 228–230° | **<br>* | 34,27<br>33,44 | 4,18<br>4,95 | 10,90<br>— | 9,20<br>9,45 | 41,45<br>40,70 | C₁₁H₁₅N₃ClBr<br>·1 HBr |
| 10 | —CH(CH₃)CH₂CH(CH₃)C₂H₅ | yes | acetic acid | 50 | 120–122° | **<br>* | 32,87<br>33,51 | 4,70<br>4,94 | —<br>— | 8,09<br>7,57 | 44,75<br>44,81 | C₁₂H₁₉N₃ClBr<br>·1,5 HBr |

\*\* = calc.
\* = found
*According to NMR spectroscopy the compound contains about 10% of an undeterminable compound as impurity As mentioned before, the effective agents may be formulated in a conventional manner as emulsion concentrates, spraying powders and dusting powders.

Here are some of the formulations used:

All percentages given by weight

| A:Emulsion Concentrate | |
|---|---|
| Effective Agent | 10 – 50% |
| Cyclohexanone | 20 – 60% |
| Xylene | 5 – 20% |
| Emulsifier IHS | 5 – 15% |

Calciumdodecylbenzolsulfonate, alkylphenol ethyleneoxidcondensates, sodiumalkylnaphtalenesulfonates, and others. Also for spraying and dusting powders, other inert ingredients may be used as fillers, for instance, talcum, magnesium carbonate, montmorillonite or china clay.

When the emulsion concentrate is made, the active agent is thoroughly mixed with the solvents in a stirrer-equipped vessel. When powder preparations are made, the dry mixture is ground to a grain size of less than 20 μ on a sledge hammer mill or other suitable grinding device, mixed once again and finally passed through a sieve.

The testing of the herbicidal properties of the below-mentioned plants are carried out after having set out the plants in dishes in a greenhouse:

Corn, barley, crab grass, wild oats, mustard, corn flower, cleavers and sugar beets.

14 days after germination, the plants were treated with 6 kg/ha of active ingredient which was formulated as emulsion concentrate (A). Evaluation occured the last time 28 days after spraying.

Table 3 shows the results:

Table 3

| Plant | Compound No. | | | | | | |
|---|---|---|---|---|---|---|---|
| | 1 | 2 | 3 | 4 | 5 | 6 | 7 |
| Corn | 2 | 0 | 0 | 0 | 4 | 4 | 0 |
| Barley | 9 | 1 | 0 | 3 | 10 | 3 | 0 |
| Crab Grass | 5 | 7 | 5 | 8 | 10 | 10 | 9 |
| Wild Oats | 7 | 6 | 10 | 6 | 10 | 10 | 10 |
| Mustard | 4 | 8 | 3 | 9 | 6 | 4 | 6 |
| Corn Flower | 3 | 8 | 2 | 7 | 10 | 6 | 8 |
| Cleavers | 7 | 7 | 10 | 6 | 10 | 10 | 10 |
| Beet | 10 | 8 | 10 | 10 | 10 | 10 | 10 |

Code:
0 = no action
10 = plants completely destroyed

In addition to the herbicidal effect, compound 5 shows fungicidal and insecticidal action.

Compound 5 has in a concentration of 2,000 ppm, a 100% effectiveness against bean rust (Uromyces phaseoli).

Compound 7 as a 0.1% spraying liquid kills red spider mites and aphids completely after 3 days.

The expert will be aware that the claimed agents can be combined with known herbicides of the class of ureas, the arylhydroxy fatty acids, the triazines, the carbamates and thiocarbamates, the dinitro alkylanilines, the acylanilides, and the dinitrophenols, to mention only the most important ones. In that manner, effectiveness can be increased or a better compatability with the cultures can be achieved. A combination with known insecticides or fungicides is likewise possible.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A compound of the formula

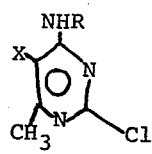

wherein X is a member of the group consisting of H and Br, and R is a member of the group consisting of straight-chain and branched-chain alkyl and cycloalkyl having from 5 to 8 C-atoms.

* * * * *